United States Patent
Casscells, III et al.

(10) Patent No.: US 7,123,968 B1
(45) Date of Patent: Oct. 17, 2006

(54) HEAT TREATMENT OF INFLAMED TISSUE

(75) Inventors: S. Ward Casscells, III, Houston, TX (US); James T. Willerson, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 09/303,313

(22) Filed: Apr. 30, 1999

Related U.S. Application Data (63) Continuation of application No. 08/934,260, filed on Sep. 19, 1997, now Pat. No. 5,906,636.

(60) Provisional application No. 60/026,418, filed on Sep. 20, 1996.

(51) Int. Cl.
*A61B 17/36* (2006.01)

(52) U.S. Cl. .......................................... 607/98; 606/27

(58) Field of Classification Search ................ 607/96, 607/97, 98, 99, 100, 101; 606/27
See application file for complete search history.

(56) References Cited

U.S. PATENT DOCUMENTS

| | | | |
|---|---|---|---|
| 3,273,395 A | 9/1966 | Schwarz | |
| 3,638,640 A | 2/1972 | Shaw | |
| 3,866,599 A | 2/1975 | Johnson | |
| 3,913,568 A | 10/1975 | Carpenter | |
| 4,005,605 A | 2/1977 | Michael | |
| 4,200,110 A | 4/1980 | Peterson et al. | |
| 4,281,645 A | 8/1981 | Jöbsis | |
| RE32,204 E | 7/1986 | Halvorsen | |
| 4,602,642 A | 7/1986 | O'Hara et al. | |
| 4,699,147 A | 10/1987 | Chilson et al. | |
| 4,752,141 A | 6/1988 | Sun et al. | |
| 4,776,334 A | 10/1988 | Prionas | |
| 4,777,955 A | 10/1988 | Brayton et al. | |
| 4,784,149 A | 11/1988 | Berman et al. | |
| 4,790,324 A | 12/1988 | O'Hara et al. | |
| 4,794,931 A | 1/1989 | Yock | |
| 4,797,840 A | 1/1989 | Fraden | |
| 4,799,479 A | 1/1989 | Spears | |
| 4,841,981 A | 6/1989 | Tanabe et al. | |
| 4,862,887 A | 9/1989 | Weber et al. | |
| 4,924,863 A * | 5/1990 | Sterzer | 606/27 |
| 4,986,671 A | 1/1991 | Sun et al. | |
| 4,995,398 A | 2/1991 | Turnidge | |
| 5,000,185 A | 3/1991 | Yock | |
| 5,046,501 A | 9/1991 | Crilly | |

(Continued)

FOREIGN PATENT DOCUMENTS

GR 649410 1/1976

(Continued)

OTHER PUBLICATIONS

The Merck Manual of Diagnosis and Therapy, section 21, chapter 291, 1995.*

(Continued)

*Primary Examiner*—Scott M. Getzow
(74) *Attorney, Agent, or Firm*—Conley Rose, P.C.

(57) ABSTRACT

The present invention relates to methods for treating inflammation in body tissues. More specifically, certain disclosed methods relate to selectively inducing apoptosis in inflammatory immune cells. The methods are particularly suitable for treating inflamed atherosclerotic plaques. The techniques generally involve heating the cells with a catheter that is equipped to produce infrared radiation. The cells are heated for a sufficient time and at a sufficient temperature to induce programmed cell death.

19 Claims, 5 Drawing Sheets
(2 of 5 Drawing Sheet(s) Filed in Color)

U.S. PATENT DOCUMENTS

| | | | |
|---|---|---|---|
| 5,057,105 A | 10/1991 | Malone et al. | |
| 5,106,387 A | 4/1992 | Kittrell et al. | |
| 5,109,859 A | 5/1992 | Jenkins | |
| 5,174,299 A | 12/1992 | Nelson | |
| 5,197,470 A | 3/1993 | Helfer et al. | |
| 5,217,456 A | 6/1993 | Narciso, Jr. | |
| 5,237,996 A | 8/1993 | Waldman et al. | |
| 5,275,594 A | 1/1994 | Baker et al. | |
| 5,279,565 A | 1/1994 | Klein et al. | |
| 5,282,813 A | 2/1994 | Redha | |
| 5,293,872 A | 3/1994 | Alfano et al. | |
| 5,304,173 A | 4/1994 | Kittrell et al. | |
| 5,313,949 A | 5/1994 | Yock | |
| 5,336,178 A | 8/1994 | Kaplan et al. | |
| 5,355,880 A | 10/1994 | Thomas et al. | |
| 5,373,849 A | 12/1994 | Maroney et al. | |
| 5,400,788 A | 3/1995 | Dias et al. | |
| 5,439,000 A | 8/1995 | Gunderson et al. | |
| 5,445,157 A | 8/1995 | Adachi et al. | |
| 5,453,448 A | 9/1995 | Narciso, Jr. | |
| 5,496,271 A | 3/1996 | Burton | |
| 5,496,311 A * | 3/1996 | Abele et al. | 606/28 |
| 5,542,915 A | 8/1996 | Edwards et al. | |
| 5,547,472 A | 8/1996 | Ohishi et al. | |
| 5,558,093 A | 9/1996 | Pomeranz | |
| 5,582,170 A | 12/1996 | Soller | |
| 5,596,995 A | 1/1997 | Sherman et al. | |
| 5,606,974 A | 3/1997 | Castellano et al. | |
| 5,611,338 A | 3/1997 | Gallup et al. | |
| 5,620,438 A | 4/1997 | Amplatz et al. | |
| 5,623,940 A | 4/1997 | Daikuzono | |
| 5,682,899 A | 11/1997 | Nashet et al. | |
| 5,708,275 A | 1/1998 | Rhodes et al. | |
| 5,733,739 A | 3/1998 | Zakin et al. | |
| 5,792,050 A | 8/1998 | Alam | |
| 5,849,028 A | 12/1998 | Chen | |
| 5,871,449 A | 2/1999 | Brown | |
| 5,924,997 A | 7/1999 | Campbell | |
| 5,935,075 A | 8/1999 | Casscells et al. | |

FOREIGN PATENT DOCUMENTS

| | | |
|---|---|---|
| WO | PCT 8911311 | 11/1989 |
| WO | PCT 9415529 | 7/1994 |
| WO | PCT 9502362 | 1/1995 |
| WO | PCT 9710748 | 3/1997 |

OTHER PUBLICATIONS

Belli, James A. et al.; Influence of Temperature on the Radiation Response of Mammalian Cells in Tissue Culture, Radiation Research, 18, 272-276 (1963).

Berliner, Judith A., et al.; Atherosclerosis: Basic Mechanisms — Oxidation, Inflammation, and Genetics, Circulation, vol. 91, No. 9, May 1, 1995, pp. 2488-2496.

Biffl, Walter L., et al.; Interleukin-6 Delays Neutrophil Apoptosis, Arch Surg/vol. 131, Jan. 1996, pp. 24-30.

Blackburn, M.J., et al.; The Sensitivity to Hyperthermia of Human Granulocyte/Macrophage Progenitor Cells (CFU-GM) Derived from Blood or Marrow of Normal Subjects and Patients with Chronic Granulocytic Leukemia, Br. J. Cancer (1984), 50, 745-751.

Buja et al.; Role of Inflammation in Coronary Plaque Disruption, pp. 503-505, Circulation, vol. 89, No. 1, Jan. 1994.

Carney et al.; Near-Infrared Spectrophotometric Monitoring of Stroke Related Changes in the Protein and Lipid Composition of Whole Gerbil Brains; Anal Chem 65:1305-13 (1993).

Casscells et al; Thermal Detection of Cellular Infiltrates In Living Atherosclerotic Plaques: Possible Implications for Plaque Rupture and Thrombosis, pp. 1447-1449 and 1422, The Lancet, vol. 347, May 25, 1996.

Cassis et al.; Near-IR Imaging of Atheromas in Living Arterial Tissue; Ana. Chem 65:1247-56 (1993).

Chen et al.; Induction of Prostaglandin Production by Hyperthermia in Murine Peritoneal Exudate Macrophages, Cancer Research 47, 11-15, Jan. 1, 1987.

Dempsey et al.; Near-Infrared Imaging and Spectrocopy in Stroke Research: Lipoprotein Distribution & Disease; Ann NY Acad Sci 820:149-69 (1997).

Elkon, et al.; Thermal Inactivation Energy of Granulocyte-Monocyte Stem Cells, Radiation Research 87, 368-372 (1981).

Ensor et al.; Warming Macrophages to Febrile Range Destablizes Tumor Necrosis Factor-$\alpha$ mRNA Without Inducing Heat Shock, pp. C1140-C1146, (1995). Am. J. Physiol 269: C1140-C1146.

Falk et al.; Coronary Plaque Disruption, pp. 657-671, Circulation, vol. 92, No. 3, Aug. 1, 1995.

Field et al.; The Relationship Between Heating Time and Temperature: Its Relevance to clinical Hyperthermia, Radiotherapy and Oncology, 1 (1983) 179-186.

Fouqueray et al.; Heat Shock Prevents Lipopolysaccharide-Induced Tumor Necrosis Factor-$\alpha$ Synthesis by Rate Mononuclear Phagocytes, Eur. J. Immunol. 1992, 22:2983-2987.

Gerweck et al.; Influence of Nutrient on Energy Deprivation on Cellular Response to Single and Fractionated Heat Treatments, Radiation Research 99, 573-581 (1984).

Hamilton et al.; Blemycin Induces Apoptosis in Human Alveolar Macrophages, Am. J. Physiol 269: L318-L325, 1995.

Haveman et al.; The Role of Energy in Hyperthermia-Induced Mammalian Cell Inactivation: A Study of the Effects of Glucose Starvation and An Uncoupler of Oxidative Phosphorylation, Journal of Cellular Physiology 107:234-241 (1981).

Kim, Young-Myeong, et al. Nitric Oxide Protects Cultured Ray Hepatocytes from Tumor Necrosis Factor-$\alpha$-Induced Apoptosis by Inducing Heat Shock Protein 70 Expression, vol. 272. No. 2. Issue of Jan. 10, pp. 1402-1411, (1997).

Kobayashi et al.; Cell Cycle-Dependent Heat Sensitization of Murine Granulocyte-Macrophage Progenitor Cells in Regenerating Marrow, Cancer Research 45, 1459-1463, Apr. 1985.

Kunkel et al.; Regulation of Macrophage Tumor Necrosis Factor Production by Prostaglandin $E_2$, Biochemical and Biophysical Research Communication, vol. 137, No. 1., May 29, 1986, pp. 404-410.

Lippman; Rapid In Vivo Quantification & Comparison of Hydroperoxides & Oxidized Collagen in Aging Mice, Rabbits & Man; Exp Geron 20:1-5 (1985).

Liu et al.; Modification of the Extracellular Matrix Following Myocardial Infarction Monitored by FTIR Spectroscopy; Biochim Biophys Acta 1315:73-77 (1996).

Mangan; Lipopolysaccharide, Tumor Necrosis Factor -$\alpha$, and IL-1$\beta$ Prevent Programmed Cell Death (Apoptosis) in Human Peripheral Blood Monocytes, The Journal of Immunology, vol. 146, 1541-1546, No. 5, Mar. 1, 1991.

Morange et al.; Interferon Pretreatment Lowers the Threshold for Maximal Heat-Shock Response in Mouse Cells, Journal of Cellular Physiology, 127:417-422 (1986).

Muller et al.; Triggers, Acute Risk Factors and Vulnerable Plaques: the Lexicon of a New Frontier, pp. 809-813, JACC, vol. 23, No. 3, Mar. 1, 1994.

Nagata et al.; The Fas Death Factor, Science, vol. 267, Mar. 10, 1995, pp. 1449-1456.

Nishina et al.; Stress0Signalling Kinase Sek 1 Protects Thymocytes From Apoptosis Mediated by CD95 and CD3, Nature, vol. 385, Jan. 23, 1997, pp. 350-353.

Ohdan et al.; New Technique Using Near-Infrared Spectroscopy for Quantifying Nitric Oxide During Acute Rejection of Liver Allograft; Transplantation 57:1674-1677 (1994).

Ohdan et al.; Simultaneous Evaluation of Nitric Oxide Synthesis & Tissue Oxygenation in Rat Liver Allograft Rejection Using Near-Infrared Spectroscopy; Transplantation 60:531-535 (1995).

Papadimitriou, J.M., et al. Quantitative Investigations of Apoptosis of Murine Mononuclear Phagocytes During Mild Hyperthermia, Experimental and Molecular Pathology 59, 1-12 (1993).

Pizurki et al.; CAMP Modulates Stress Protein Synthesis in Human Monocytes, Macrophages, Journal of Cellular Physiology, 161:169-177 (1994).

Prins et al.; Apoptosis of Human Adipocytes in Vitro, Biochemical and Biophysical Res. Communications, vol. 201, No. 2, (1994), pp. 500-507.

Reddy et al.; Heat Shock Treatment of Macrophages Causes Increased Release of Superoxide Anion, Infection and Immunity, Jun. 1992, vol. 60, No. 6, pp. 2386-2390.

Ribeiro et al.; Effects of the Stress Response in Septic Rats and LPS-Stimulated Alveolar Macrophages: Evidence for TNF-α Post-translational Regulation, Am J Respir Crit Car Med 1996: 154: 1843-1850.

Robinson et al.; Noninvasive Glucose Monitoring in Diabetic Patients: A Preliminary Evaluation; Clin Chem 38:1618-1622 (1992).

Sivo et al.; Heat Shock Mimics Glucocorticoid Effect on IFN-γ-Induced FcγRI and Ia Messenger RNA Expression in Mouse Peritoneal Macrophages, the Journal of Immunology, 1996, pp. 3450-3454.

Snyder Yvonne M., et al. Transcriptional Inhibition of Endotozin-Induced Monokine Synthesis Following Heat Shock in Murine Peritoneal Macrophages, Journal of Leukoctye Biology, vol. 51, Feb. 1992, pp. 181-187.

Thompson, Craig B. Apoptosis in the Pathogenesis and Treatment of Disease, Science, vol. 267, Mar. 10, 1995, pp. 1456-1462.

van der Wal et al., Site of Intimal Rupture or Erosion of Thrombosed Coronary Atherosclerotic Plaques: Is Characterized by An Inflammatory Process Irrespective of the Dominant Plaque Morphology, pp. 36-44, Circulation, vol. 89, No. 1, Jan. 1994.

Vaux, D.L., et al. The Molecular Biology of Apoptosis, Proc. Natl. Acad. Sci. USA, vol. 93, pp. 2239-2244, Mar. 1996.

Verheji et al.; Requirement for Cereamide-Initiated SAPK/JNK Signalling in Stress-Induced Apoptosis, Nature, vol. 380, Mar. 1996, pp. 75-79.

Wang et al.; Induction of Heat Shock Protein 72 Prevents Neutrophil-Mediated Human Endothelial Cell Necrosis, Arch Surg/ vol. 130, Dec. 1995, pp. 1260-1265.

Wang et al.; Induction of Human Endothelial Cell Apoptosis Requires Both Heat Shock and Oxidative Stress Responses, Am. J. Physiol. 272, 1997, pp. C1543-C1551.

Westra et al.; Variation in Sensitivity to Heat Shock During the Cell-Cycle of Chinese Hamster Cells In Vitro, Int. J. Radiat. Biol., 1971, vol. 19, No. 5, pp. 467-477.

Wike-Holley et al.; The Relevance of Tumour pH to the Treatment of Malignant Disease, Radiotherapy and Oncology, 2 (1984) 343-366.

* cited by examiner

HEAT TREATMENT OF INFLAMED TISSUE

CROSS-REFERENCE TO RELATED APPLICATION

This is a continuation of application Ser. No. 08/934,260, filed Sep. 19, 1997, now U.S. Pat. No. 5,906,636, which was an application converted from provisional Application 60/026,418, filed Sep. 20, 1996.

STATEMENT REGARDING FEDERALLY SPONSORED RESEARCH OR DEVELOPMENT

Not applicable.

BACKGROUND OF THE INVENTION

A. Field of the Invention

This invention relates to the treatment of harmful inflammation in body tissue by exposing the inflammatory cells to heat. In one method, heat is applied to an inflamed atherosclerotic plaque by means of a catheter that is equipped with a heating source. Such heating can be very mild (38° C.–40° C.) so as to quiesce macrophages and other inflammatory cells, or moderate (41°–44° C.) to induce programmed cell death, apoptosis, but not hot enough to cause necrosis and subsequent inflammation.

B. Description of Related Art

Coronary artery disease is a leading cause of death in industrialized countries. It is manifested by athersclerotic plaques, which are thickened areas in vessel walls. A plaque is an accumulation of cholesterol, proliferating smooth muscle cells and inflammatory cells covered by cellular secretions of collagen that form a cap over the plaque in the vessel wall. Macrophages migrate into and accumulate in a plaque causing inflammation. Inflamed plaques are most susceptible to ruptures and the formation of blood clots. Falk, E. (1995).

Atherosclerotic plaques are thought to develop in response to irritation or biochemical damage of the endothelial cells that line blood vessel walls. Agents that are known to damage these cells include cigarette smoke, high serum cholesterol (especially in the form of oxidized low density lipoprotein), hemodynamic alterations (such as those found at vessel branch points), some viruses (herpes simplex, cytomegalovirus) or bacteria (e.g., Chlamydia), hypertension, and some plasma hormones (including angiotensisn II, norepinephrine) and homocysteine. Atherosclerotic plaques grow slowly over many years in response to the cumulative injury of endothelial cells. Ross (1993), Berliner (1995).

Typically, several dozen plaques are found in arteries afflicted with this disease. It is the rupture of these plaques that brings about the terminal stage of the disease. The rupture causes a large thrombus (blood clot) to form on the inside of the artery, which may completely occlude the blood flow through the artery, thereby injuring the heart or brain. Falk, E. (1995).

In most cases of terminal coronary artery disease, only one of several plaques ruptures. Rupture typically is caused by inflammatory cells, primarily macrophages, that lay beneath the surface collagen layer of the plaques. These cells release enzymes that tend to degrade the cap. Once a plaque ruptures, blood clots are formed and it is these clots that are believed to be responsible for over one half of all heart attacks and stokes. Falk, E. (1995); Buja (1994).

Techniques have been developed to identify those plaques that are most likely to rupture because of inflammation. See U.S. patent application Ser. No. 08/717,449, which is specifically incorporated by reference herein. The most common treatment for these plaques is balloon angioplasty. However, this method is known to result in about a 5% incidence of complete thrombotic occlusion and a 30–40% incidence of vessel reclosure due to restenosis. It is clear that in many cases balloon angioplasty causes cellular injury and only temporarily eliminates the danger from an inflamed plaque until the advent of a secondary inflammatory response. Casscells (1994).

It has been shown that macrophages have a life span of only about a week or two in the vessel wall. Katsuda (1993). Typically, monocytes enter the atherosclerotic plaque, divide once, and contribute to plaque development by their ability to oxidize low density lipoprotein cholesterol and to release factors which cause smooth muscle proliferation and angiogenesis. The cells then undergo apoptosis, which is an active process of programmed cell death. This process differs from necrosis in that apoptosis requires the expenditure of energy, and the synthesis of new RNA and proteins in all but the inflammatory cells, the active cleavage of DNA and the shrinkage and involution of the cell with very little inflammation. Steller (1995); Nagata (1995); Thompson (1995); Vaux (1996).

Apoptosis is a form of programmed cell death in which the dying cells retain membrane integrity and are rapidly phagocytosed and digested by macrophages or by neighboring cells. It occurs by means of an intrinsic cellular suicide program that results in DNA fragmentation and nuclear and cytoplasmic condensation. The dead cells are rapidly cleared without leaking their contents and therefore little inflammatory reaction follows. It can be induced by the withdrawal of growth factors and to some extent by factors which can also cause necrosis such as extreme lack of oxygen or glucose, heat, oxidation and other physical factors.

Previously no method was known for selectively inducing apoptosis in macrophages or other inflammatory cells in a blood vessel without also inducing apoptosis in beneficial endothelial cells. Known methods for inducing apoptosis were systemic, including treatments with chemicals and elevated temperatures. Such methods are not useful as therapeutic methods because of the risk that apoptosis will develop in healthy tissue.

A number of studies have shown that heat can induce programmed cell death. Kunkel (1986) have found that indomethacin inhibits macrophage synthesis of prostaglandin but enhances macrophage production of TNF-α, which suggests that heating may have advantages over indomethacin as an anti-inflammatory treatment. Preventing the synthesis of prostaglandin, which serve as feedback inhibitors of macrophage function, limits the anti-inflammatory utility of indomethacin and presumably other inhibitors of cyclooxygenase. Field and Morris (1983) surveyed many cell types and found that the time needed to kill cells at 43° C. varied from four minutes in mouse testis, to 32 minutes in rat tumor 96 in vivo, to 37 minutes for mouse jejunum, to 75 minutes for rat skin, 210 minutes for mouse skin and 850 minutes for pig skin. Numerous other cell types were also studied. They observed that, above 42.5° C., an increase of 1° C. produces a similar effect as doubling the duration of heat exposure. Wike-Hooly (1984) found that a low pH enhanced hyperthermic cell killing, as did a low glucose or insulin exposure and that nitroprusside also increased the cell mortality caused by hyperthermia. Raaphorst (1985) and Belli (1988) studied Chinese hamster lung fibroblasts and found that 45° C. heat and radiation were synergistic in cell killing. Raaphorst (1985) also found S-phase to be heat-sensitive and least radiosensitive, while in G1 and G2 the opposite was true. Klostergard (1989) found that cytotoxicity of macrophages was decreased by heating to 40.5° C. for 60 minutes. Westra and Dewey (1971) found that in CHO cells S phase was more sensitive to heating to 45.5° C. than was G1 phase. M phase was intermediate. In contrast, radiation killed cells preferentially in phases G1 and M1. Fifty percent of asynchronous (cycling) CHO cells were killed by a 20 minute heat treatment at 43.5° C. Freeman (1980) found that the sensitivity of CHO cells to 41° C. to 45.5° C. was increased with acidosis and that thermotolerance was induced by exposure to 42° C. for 250 minutes. Haverman and Hahn (1982) used an inhibitor of oxidative phosphorylation and found that CHO cells were thereby more prone to heat-induced death using 43° C. for one hour. Preheating, however, led to tolerance. These experiments could not determine whether hyperthermia increased ATP utilization or inhibited its synthesis. Gerweck (1984) found that CHO cells were more easily killed by 44° C. (20% died after a 15-minute exposure) when ATP was depleted by hypoxia and hypoglycemia, but neither condition alone had an effect. Lavie (1992) found that peritoneal macrophages from older mice tend to die at 42.5° C. for 20 minutes but not macrophages from younger mice. Papdimitriou (1993) found that most peritoneal murine macrophages undergo apoptosis with a five-hour exposure to 41° C., but few entered apoptosis at 30° C. Most circulating monocytes did not undergo apoptosis at 41° C., with a five-hour exposure. Mangan (1991) reported that TNF alpha and interleukin-1 beta prevent macrophage apoptosis. Chen (1987) reported that heat in the range of 41° C. to 43° C. stimulated macrophage production of prostaglandins. Prostaglandins serve to suppress macrophage production and phagocytosis. Heat did not decrease prostaglandin release from tumor cell line or from fibroblasts. They found that macrophage death began at 41° C. with a four-hour exposure. A six-hour exposure to 43° C. killed half the macrophages. Ensor (1995) found no macrophage cell death after six hours at 40° C., (vs. 37° C.) but at 43° C. only 4% of cells were viable at six hours. O'Hara (1992) found that bone marrow macrophages survive 15 minutes at 45° C. if they have been preheated for 110 minutes to 42.5° C. Fouqueray (1992) found that exposing rat peritoneal macrophages to 39° C. to 41° C. for 20 minutes decreased synthesis of IL-1 and TNF-α. Circulating monocytes were less sensitive to heat than glomerular or peritoneal macrophages. This degree of heating did not kill the macrophages. Hamilton (1995) found that the cancer drug bleomycin blocked expression of HSP-72 in human alveolar macrophages in response to exposure to 39.8° C. This was a relatively specific effect since there was no change in overall protein synthesis and, moreover, the effect appeared to be post-transcriptional, since there was no change in mRNA levels for HSP-72. The bleomycin exposure did not cause much necrosis, but it caused marked DNA fragmentation characteristic of apoptosis. Wang (1995) found that induction of HSP-72 prevented necrosis in human endothelial cells exposed to activated neutrophils. The activated neutrophils caused necrosis of endothelial cells that had been exposed to 30 to 60 minutes of heat shock at 42° C., an exposure which by itself did not induce necrosis or apoptosis. Wang (1997) found that endothelial cells did not go to apoptosis with a 45-minute exposure to 42° C. or with exposure to TNF-α, but exposure to both did trigger apoptosis. TNF-α resulted in generation of reactive oxygen species, which the authors believe may be required, together with heat shock, to induce apoptosis in endothelial cells. Kim (1997) found that nitric oxide protected cultured rat hepatocytes from TNF-α induced apoptosis by means of inducing HSP-70. Belli (1963) observed that heating enhances cell susceptibility to radiation killing.

Cytokines are also known to influence apoptosis in macrophages and other leukocytes. William (1996) found that apoptosis in neutrophils was promoted by heat, TNF-α, or endotoxin but inhibited by LPS, GMCSF and IL-2. Biffl (1996) found that IL-6 also delayed neutrophil apoptosis. Prins (1994) found in human fat tissue explants adipocytes underwent apoptosis within 24 hours of a 60-minute exposure to 43° C. and then underwent phagocytosis, suggesting that at least some macrophages survived longer than some adipocytes. O'Hara (1992) showed that granulocyte-macrophage precursors take longer ($T_{1/2}$=36 min.) to become heat-tolerant than do stem cells or erythrocyte precursors from bone marrow. Verhelj (1996) found that 50 percent of confluent, nondividing, bovine aortic endothelial cells underwent apoptosis by 12 hours at 43° C., versus 41° C. for dividing human monoblastic leukemia of the U937 line, but this difference could well be attributable to the difference in age of the cells, cycling rate or species. D. Elkon and H. E. McGrath (1981) presented some evidence that granulocyte monocyte stem cells do not take as long as other cells to be killed at a temperature of 42.5° C. Blackburn (1984) reported that circulating monocyte precursors are more sensitive to heat than are those from bone marrow. Kobayashi (1985) reported that granulocyte-macrophage progenitor cells were more sensitive to 60 minutes at 42° C. when the marrow was regenerating (during cell division) than when it was stationary, but this is a finding in all cell types. Cohen (1991) found no difference in heat tolerance of epithelial cells and airway macrophages, as measured by immediate release of LDH and chromium-51.

A number of studies have studied the relationship between heat shock and cell killing. Nishina (1997) found that the stress-activated protein kinases (also known as the Jun N-terminal kinases) are activated in response to heat shock and other cell stresses. A knockout of one of these genes (SEK-1) resulted in fewer CD4+, CD8+ thymocytes. Pizurki and Polla (1994) found that cAMP increased synthesis of heat-shock proteins by heated macrophages. Reddy (1982) found that heat shock of murine macrophages increased their production of superoxide but did not change their production of hydrogen peroxide or their microbicidal activity. Sivo (1996) found that heat shock acted in a fashion similar to glucocorticoids in inhibiting mouse peritoneal macrophages and increased the transfer of glucocorticoid receptors to the nucleus. Snyder et. al (1992) found that mouse peritoneal macrophages synthesized heat-shock proteins (HSPs) maximally after a 12-minute exposure to 45° C.; HSPs were only found two to six hours after heat treatment. They found no HSP-70 at 42° C. or 43° C. At 2 and 24 hours after heating, phagocytosis was normal. They did not mention whether macrophages entered apoptosis with this treatment and that the same treatment (12 minutes at 45° C.) decreased TNF alpha and IL-1 RNA synthesis in mouse peritoneal macrophages. Pizurki et. al (1994) reported that circulating human monocytes express HSPs two hours after 20 minutes of exposure of 45° C. and that expression was enhanced in cAMP and unaffected by indomethacin.

A number of studies have shown that heating and chemical treatments change the activity of immune cells. Chen (1987) found that heating murine macrophages to 41° C. to 43° C. for one hour caused them to synthesize and release prostaglandins of the E type. Fouqueray (1992) found that a 20-minute exposure of rat peritoneal macrophages to 39° C. to 41° C. decreased synthesis of tumor necrosis factor alpha and interleukin-1 within two hours, but monocytes circulating in the blood were less sensitive to heating than were the tissue macrophages. Ribeiro (1996) confirmed that heat exposure decreases macrophage release of TNF alpha both in vitro and in vivo. Kunkel (1986) showed that indomethacin inhibited lipopolysaccharide (LPS)-induced synthesis of prostaglandins by macrophages (and inhibited heat-induced PGEs Chen, 1987) but enhanced macrophage production of TNF-α in response to LPS. Morange M. (1986) found that HSPs were induced at lower temperatures when cells were exposed to interferon-alpha and interferon-beta. Ensor (1995) reported that exposing a macrophage cell line to 40° C. for 30 minutes prevented (within six hours) synthesis and release of TNF-α in response exposure to LPS. The half-life of TNF-α mRNA was shortened. There was no change in the levels of mRNA for GAPDH, β-actin or IL-6. HSP-72 was increased at 43° C. The same authors previously showed that in human macrophages TNF expression was suppressed at 38.5° C., but HSP-72 was increased only above 40° C. Papadimitriou showed that macrophage apoptosis was minimal at 39° C. but substantial at 41° C.

Although the cellular phenomenon of apoptosis has been studied in some detail in tissue culture, no studies have been directed toward developing that technique for the treatment of inflammation. New methods are needed for treating inflamed body tissues and in particular to the treatment of atherosclerotic plaques to prevent rupture. Such methods should not induce an inflammatory response and should be capable of eliminating or neutralizing macrophages or other inflammatory cells without damaging blood vessel walls. Novel methods for selectively inducing apoptosis are also needed. Such methods will be useful in preventing the rupture of atherosclerotic plaques and therefore reduce the risk of death from myocardial infarction or stroke.

BRIEF SUMMARY OF THE INVENTION

The present invention provides novel methods that can be used to treat inflammation in body tissues and in particular to treat inflamed atherosclerotic plaques. The methods can be used to decrease or eliminate inflammation in a plaque to prevent rupture. Certain disclosed methods are particularly useful for inducing apoptosis in localized cell clusters such as the macrophages that cause an inflammatory response.

The present methods utilize localized and mild hyperthermic treatments to neutralize or preferably to induce apoptosis in inflammatory cells. Localized heat treatments avoid systemic cell damage and at the same time lead to clearance of unwanted cells without causing a secondary inflammation.

The techniques disclosed herein are useful in the treatment of inflammation. The term inflammation includes inflamed atherosclerotic plaques; restenosis; and arteritis such as that found in systemic lupus, Takayasu's arteritis, Beheet's syndrome, temporal (gran+ cell) arteritis, myocarditis of the autoimmune etiology; arteriovenous fistulea, dialysis grafts or other vascular prosthesis. The phrase "treating inflammation" also includes treating a region of a vein prior to or after balloon angioplasty, rotational or directional atherectomy, stenting or related interventions that could result in inflammation and subsequent thrombosis, acute closure or restenosis. Use of the disclosed methods on atherosclerotic plaques will reduce the chance of myocardial infarction or stroke.

Certain methods of the present invention are useful for inducing apoptosis in inflammatory cells. Inflammatory cells primarily consist of macrophages and other closely related cells of the immune system that are involved in creating inflammation. The present methods specifically contemplate inducing apoptosis in these cells with hyperthermic treatments.

Some of the present methods are directed to treating inflamed regions containing deleterious immune cells with heat in the range of 38.5° C.–44° C. for between about 5 minutes to 60 minutes and more typically for at least about 15 to 30 minutes. At the high end of the temperature range, from about 41° C. to 44° C., apoptosis is more effectively induced. Temperatures above 44° C. are not preferred because they begin to cause cell killing through necrosis and pathways that cause secondary inflammation. Treatments at the low end of the temperature range may also be effective. For example, heating with temperatures in the range of 38.5° C. to 40° C., which are below those necessary to cause apoptosis on brief exposures (e.g., 15 minutes) can be used to decrease macrophage production and their release of cytokines. These temperatures are contemplated to be within the present invention. Generally, temperatures of approximately 42° C. to 43° C. will be used.

In patients, following routine angiography, a heat detecting probe, such as is described in U.S. patent application Ser. No. 08/717,449, would be used to identify lesions that are significantly hotter than the rest of the artery. Lesions at higher risk of rupture are about two degrees warmer than adjacent tissue. These lesions are detectable by heat imaging catheters consisting of any of several fibers that conduct heat, bundled into a standard coronary or other angiographic catheter ranging from 4 French to 14 French in diameter. Alternatively, a catheter with standard heat sensing electrodes on its surface could be used. In one embodiment, this would be a balloon catheter made of a compliant (soft) balloon material, so as not to damage the endothelium or disrupt the plaque itself.

Heat may be transferred to the target cells by a variety of methods. In preferred methods, heat is transferred into an inflamed plaque in a blood vessel by means of a catheter. Several catheters are commercially available that are capable of introducing the heat required for these techniques. In addition, the catheter disclosed in U.S. patent application Ser. No. 08/717,449 can easily be equipped to emit infrared radiation by one of skill in the catheter arts. Preferred catheters are those that can deliver heat within the temperature range of 38.5–44° C. Catheters that emit heat above about 45° C. are not preferred because the use of such elevated temperatures may damage endothelial cells and produce a secondary inflammatory response.

Heat can also be introduced into a region of inflamed tissue by introducing a stent into the lumen of a blood vessel or the lumen of an organ to treat inflammation in blood vessels, parenchymal smooth muscle cells or interstitial cells such as fibroblasts to prevent obstruction and/or thrombosis in the lumen. Methods for positioning stents are well known in the art. The stent is positioned in such a way as to be in thermal contact with a region of inflamed tissue. The stent is then heated. It can be heated electrically or with microwave or radio frequency radiation or other means. These heating methods can be produced from devices such as catheters within the lumen or from energy sources such as radiofrequency sources outside the body. It would be clear to one of skill in the art that the stent used in such an application must be able to transmit heat. The preferred stents are made of metal.

Other methods for heating inflamed tissue are also contemplated in this invention. For example heat can be transferred into inflamed tissues and plaques by flushing the inflamed tissue with a liquid such as a saline or other solution. The solution can be passed into the lumen of a blood vessel, for example, through a catheter and delivered directly to the inflamed plaque or tissue. Heating of the liquid can be accomplished by well known methods before or during passage into the inflamed tissue.

Although the present techniques primarily rely upon heating methods, chemical agents or radiation may also be employed to augment the effectiveness of heat treatments. For example, beta-blocking drugs, cytokines such as insulin-like growth factor, transforming growth factor B1, vascular endothelial growth factor, fibroblast growth factor, tumor necrosis factor and the like may be used to enhance the susceptibility of macrophages to heat induced apoptosis or to increase the resistance of endothelial cells to apoptosis. Effective amounts of these drugs can easily be determined by one of skill in the art.

BRIEF DESCRIPTION OF FIGURES

The patent or application file contains at least one drawing executed in color. Copies of this patent or patent application publication with color drawings will be provided by the Office upon request and payment of the necessary fee.

DETAILED DESCRIPTION OF THE PREFERRED EMBODIMENT

The following examples are offered by way of illustration and are not intended to limit the invention in any manner. In the examples, all temperatures are in degrees Celsius unless otherwise noted.

EXAMPLE I

The inventors have made the surprising discovery that macrophages are more susceptible to heat induced apoptosis than endothelial cells. This discovery led to the development of the present techniques that use heat to reduce inflammation in inflamed tissue and especially in inflamed atherosclerotic plaques. However, greater sensitivity to heat-induced apoptosis of macrophages is not a requirement of the invention because many athersclerotic plaques are denuded of endothelium in which case induction of endothelial cell apoptosis would be moot.

Figure 1:
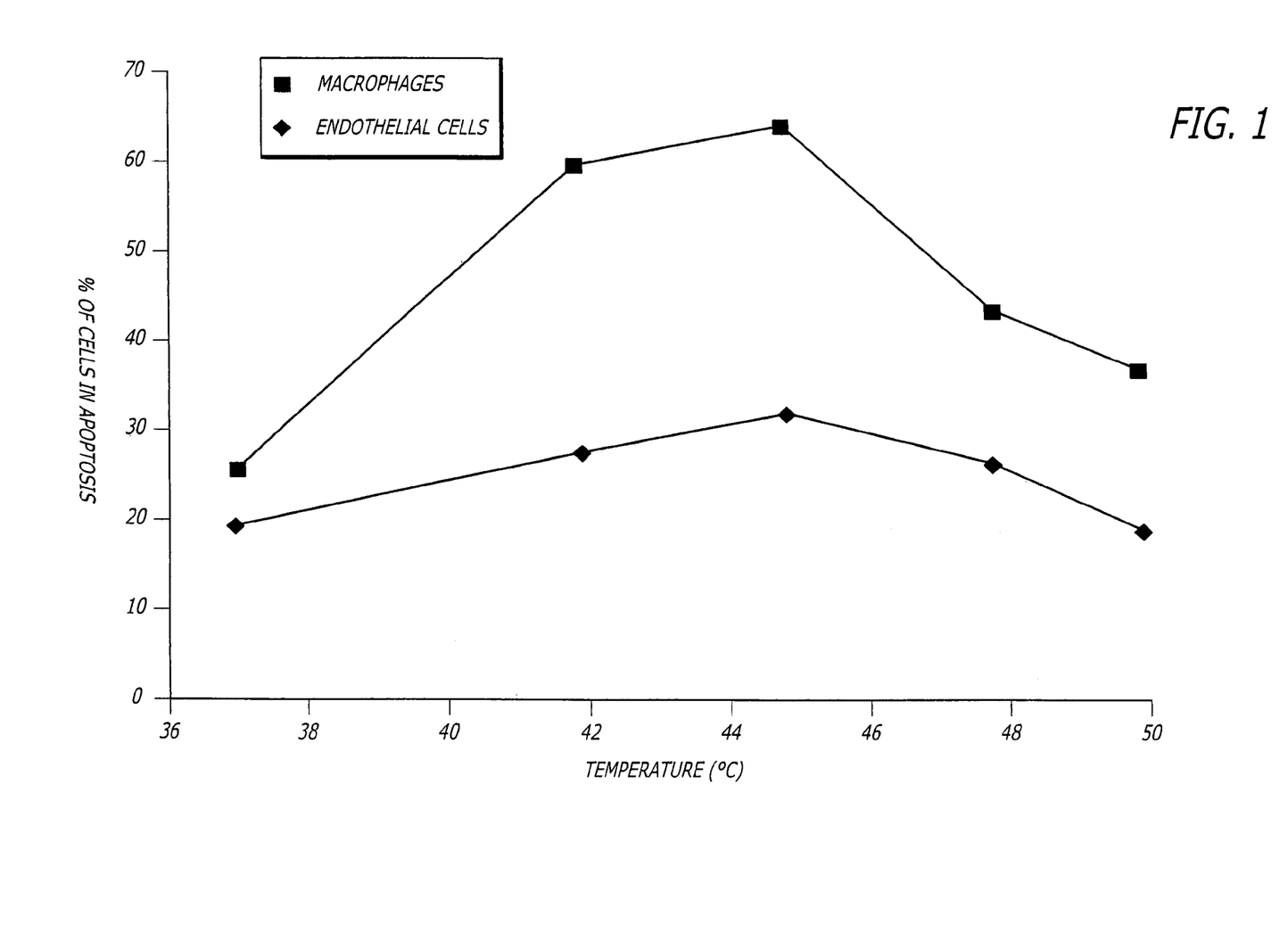
FIG. 1. Graph showing the percent of cells from Watanabe (atherosclerosis) rabbit aorta tissue undergoing apoptosis after exposure for 15 minutes at the temperatures shown.
Figure 2:
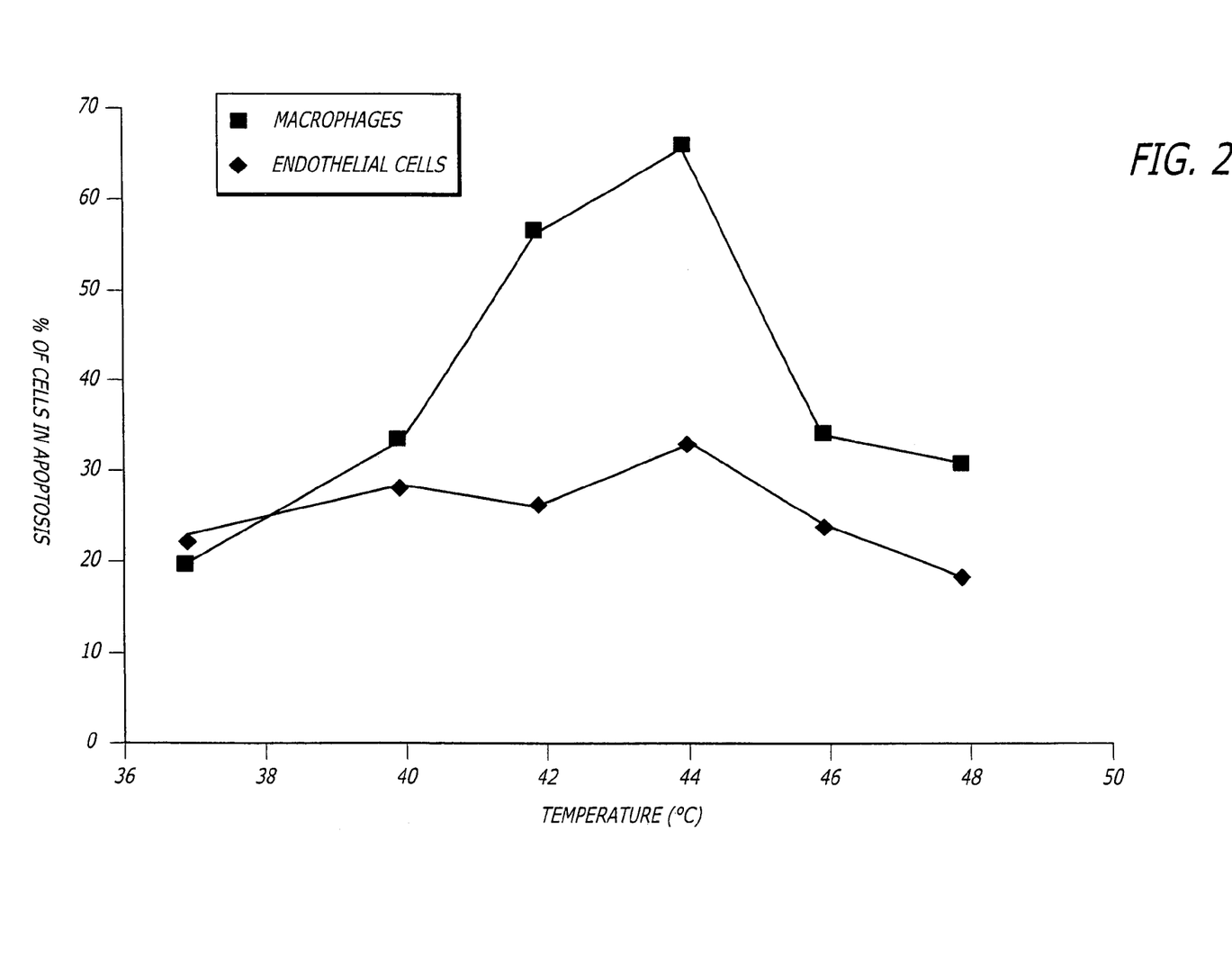
FIG. 2. Graph showing the percent of cells in apoptosis from human endarterectomy tissue after heating in cell culture for 15 minutes at the temperatures shown.

FIG. 1 shows the percent of cells from Watanabe (atherosclerosis) rabbit aorta tissue undergoing apoptosis after exposure for 15 minutes at the temperatures shown, followed by "TUNEL" staining after a 6 hour incubation at 37° C. FIG. 2 shows similar results when the cells in human carotid artery endarterectomy samples were investigated in a similar manner. Living human carotid atherosclerotic plaque was obtained by endarterectomy, immediately placed in tissue culture and subjected to varying temperatures for fifteen minutes. After four subsequent hours at 37° C. these specimens were-fixed and processed for light and electron microscopic histology. The sections were subjected to histochemistry for the enzyme terminal deoxynucelotidyl transferase, which results in a blue color in the apoptotic cell. A kit from Trevigen, Inc (Gaithersburg, Md., 20877) was used with the appropriate positive and negative controls. As a further control the stained cells were evaluated by electron microscopy. The results show a significant number of apoptotic cells at 37° C. There was an increase in the number of apoptotic cells at 42° C. with a peak at 45° C.

These results were confirmed by electron microscopic finding of chromatin margination, protrusions and nuclear fragmentation and budding with the production of membrane bound apoptotic bodies. Light microscopy suggested that almost all of the cells undergoing apoptosis were macrophages. Finally, a minority of endothelial cells underwent apoptosis with 15 minutes of exposure to 45° C., suggesting that there is indeed a window in which the macrophages can selectively be induced to undergo apoptosis.

Figure 3:
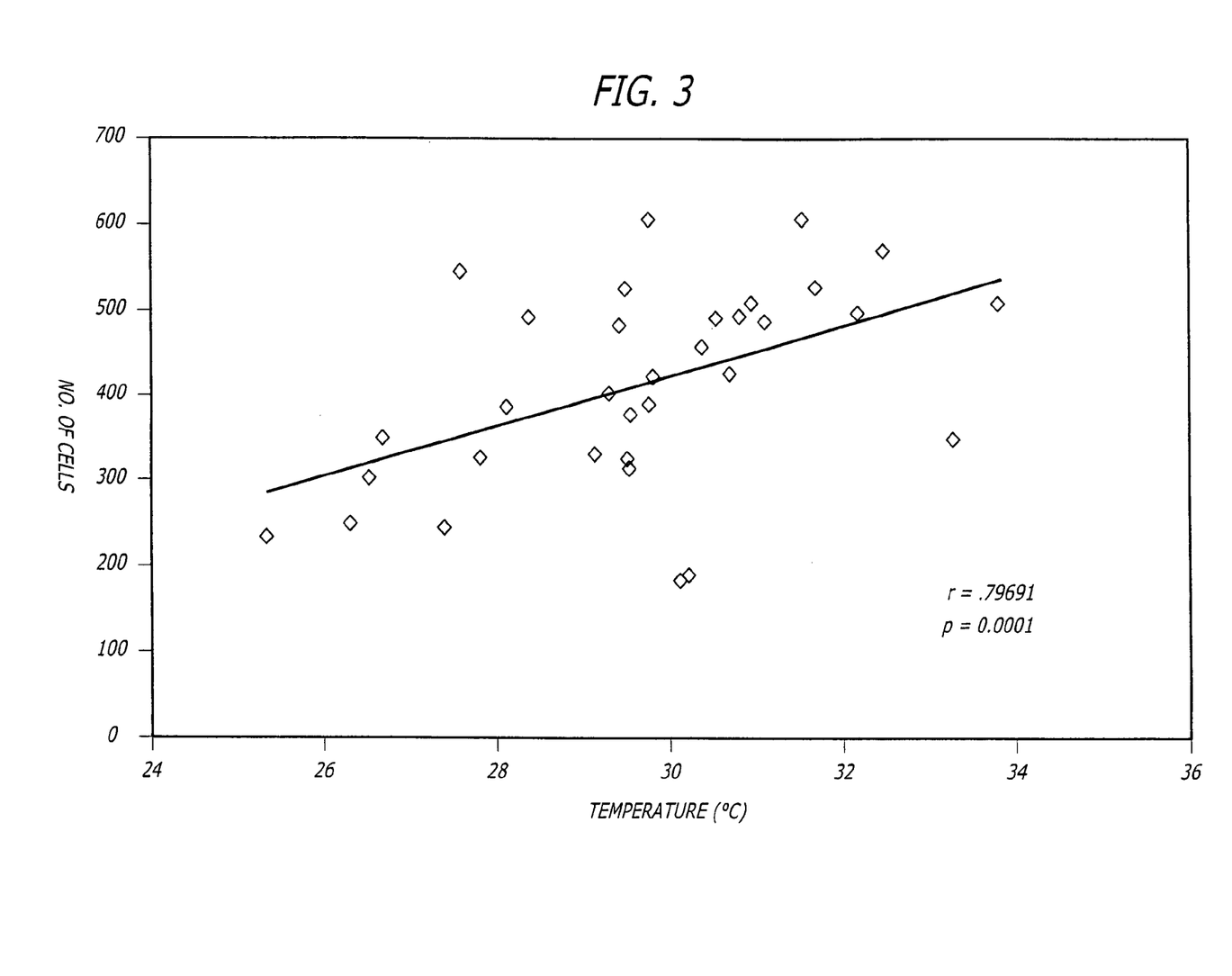
FIG. 3. Graph showing relationship of heat as measured by infrared camera, to cell density in living-human carotid endarterectomy specimens.
Figure 4A:
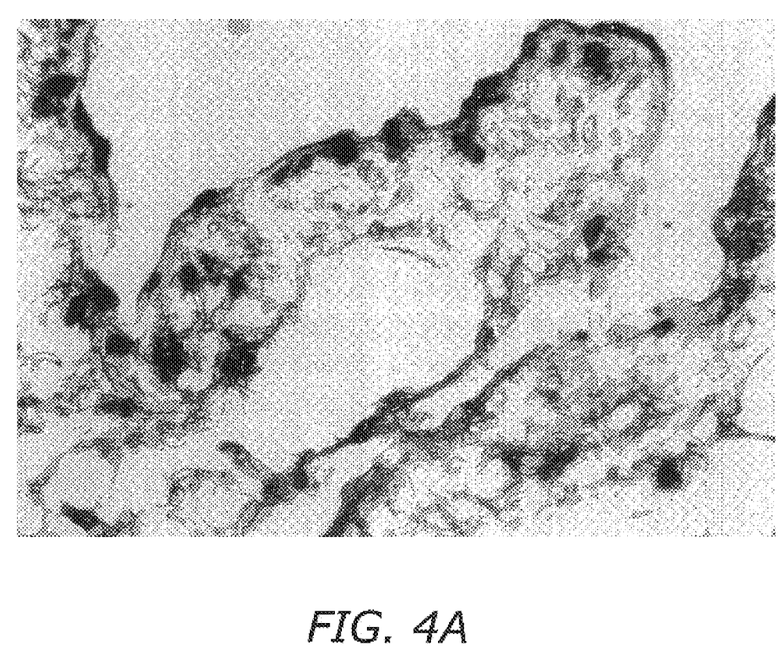
FIGS. 4A, B Photomicrograph of a representative specimen of human carotid endarterectomy tissue half (A) of which was heated to 44° C. for 15 minutes.
Figure 4B:
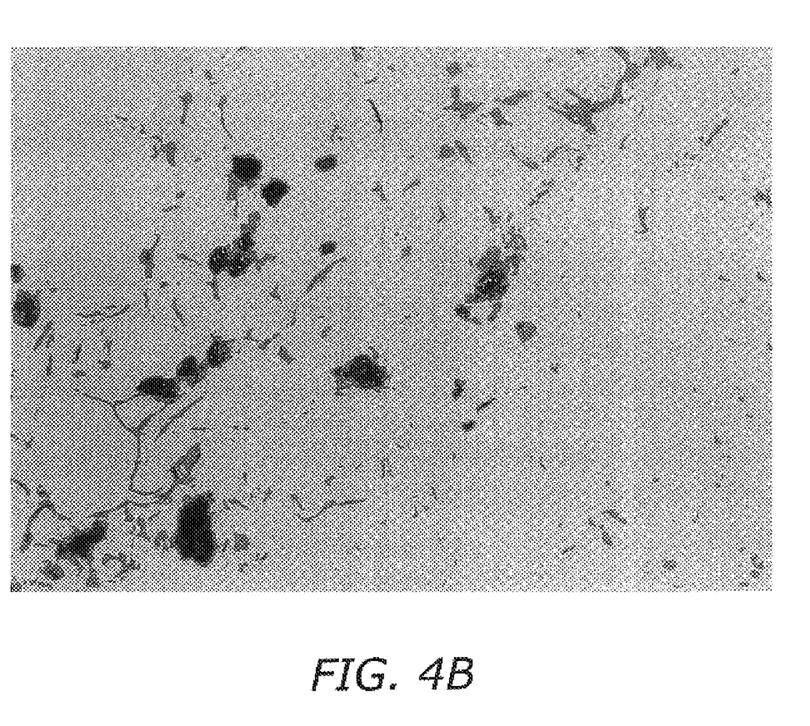

FIG. 3 shows more directly the relationship between cell density and heat produced as measured by an infrared camera. The elevated heat produced in areas having elevated numbers of macrophages facilitates a detection method for identifying inflamed plaques as discussed in U.S. patent application Ser. No. 08/717,449. In FIGS. 4A and 4B is shown the results from a study in which a representative specimen of human carotid endarterectomy tissue was divided and half incubated at 44° C. for 15 minutes in a humidified incubator, followed by 6 hours at 37° C. "TUNEL" staining for DNA was employed to demonstrate apoptosis. These cells are indicated by the dark stain. No counterstain was used in this section. The capillary nuclei are faintly shown as unstained macrophage nuclei. The photograph demonstrates the difference between the nuclei of heated (FIG. 4A) and unheated (FIG. 4B) cells.

EXAMPLE II

Treatment of Inflamed Plaques

Typically, heat induced apoptosis of inflammatory cells to prevent rupture and/or thrombosis of atherosclerotic plaques in the coronary, carotid, iliac femoral or superficial femoral arteries will be carried out in patients presenting with symptoms of ischemia. For example, patients with angina or a positive stress test, or patients with a recent myocardial infarction who are undergoing coronary angiography, will have an infrared catheter passed down the artery in a fashion similar to that of intravascular ultrasound or angioscopy, as described further below.

Some patients will be referred for this procedure for other reasons. For example, patients having plasma that shows biochemical evidence of inflammation or thrombosis, or endothelial damage or silent myocardial damage, may require coronary catheterization. Alternative tests which might bring non-symptomatic people to coronary angiography and infrared testing might include a magnetic resonance imaging scan which can give a kind of non-invasive thermometry, or positron emission tomography, which gives a non-invasive image of glucose utilization (this may indicate macrophage presence because of their high glucose consumption when activated).

The patients who come for peripheral angiography come either because of claudication or embolism to the feet or because a doctor has found diminished pulses on physical examination. Patients requiring carotid angiography typically have had a stroke or transient ischemic attack or a bruit has been detected on physical examination or a carotid narrowing has been-detected in the course of magnetic resonance imaging, Doppler imaging or angiography performed for other reasons.

In the patients described above, following routine angiography, a heat detecting probe, such as is described in U.S. patent application Ser. No. 08/717,449, will be used to identify lesions that are significantly hotter than the rest of the artery. Lesions at higher risk of rupture are two degrees warmer than adjacent tissue. These lesions could be detected by an imaging catheter consisting of any of several fibers that conduct heat, bundled into a standard coronary or other angiographic catheter ranging from four French to seven French in diameter. Alternatively, a catheter with standard electrodes on its surface could be used. In one method this will be a balloon catheter made of a compliant (soft) balloon material, so as not to damage the endothelium or disrupt the plaque itself.

Additional evidence that a particular lesion may pose a high risk to the patient, even though the stenosis may be no more than twenty or thirty percent in cross sectional diameter, may be provided by other techniques such as intravascular ultrasound (to determine how thin the fibrous cap is) optical coherence tomography which detects cracks in the plaque surface, and/or angioscopy which detects superficial thrombosis.

Treatment of an inflamed lesion will be performed in several ways. One method is to gently heat the inflamed tissue with heat from about 38.5° C. to approximately 44° C. The treatment is gentle so as not cause cell death due to protein denaturation, desiccation, vesication and/or necrosis. This heating step will be carried out for approximately 15 minutes. This treatment will trigger programmed cell death (apoptosis) in the inflammatory cells and spares endothelial cells. A catheter equipped to radiate heat will be used in this method by placing the tip at the location of the "hot" plaque and directing heat into the plaque. Subsequently, thermography can be repeated to determine the success of the treatment.

Lower amounts of heat will also be used to treat inflamed tissue. For example, heating to 38.5° to 41° (which induces apoptosis in a smaller percentage of macrophages) will have the beneficial effect of decreasing inflammation produced by macrophages by reducing the production of cytokines such as interleukin 1 and interferon gamma. Likewise heating times can be varied. Thus, it is envisioned that some treatments will be for approximately 60 minutes, particularly when lower temperatures will be used. In some cases heating times may be as short as 5 minutes, especially when higher temperatures will be used.

Adjunctive treatments will include the use of cytokines that are known to deactivate macrophages. Examples of cytokines envisioned for these treatments include TGF-B1 and TNF-α. Other adjunctive therapies will be those directed to preventing the attachment of cytokines to their receptors, the attachment of monocytes, lymphocytes or neutrophils to cells, the expression of selectins or cytokines or chemotactic factors by endothelial cells, soluble receptors and other antagonists of inflammatory cytokines and chemotactic factors, as well as chemical treatments that destroy inflammatory cells.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, a catheter equipped with a laser or other heat source can be substituted for a catheter that produces infrared radiation. In addition, this technique could be adapted to prevent or delay the onset of tissue rejection and treatments of other inflamed tissues, such as restenosis after balloon angioplasty; or related interventions including stenting and rotational or directional atherectomy (since macrophage density in these tissues predicts restenosis (Moreno) elimination of macrophages by heat-induction of apoptosis will reduce the likelihood that restenosis will occur). Another application will be stenosis of arteriovenous fistulae, dialysis grafts, and other vascular prostheses. In these applications, heat therapy can be applied either from within the vessel or across the skin by means of infrared radiation, radiofrequency, heated metal, etc. Still another application would be the use of microwave or radiofrequency to preferentially heat a metal stent to induce macrophage apoptosis to prevent stenosis or resterosis. All such modifications are intended to be included within the scope of the appended claims.

REFERENCES CITED

The following references to the extent that they provide procedural details supplementary to those set forth herein, are specifically incorporated herein by reference.

Belli J A and Bonte F J. Influence of temperature on the radiation response of mammalian cells in tissue culture. *Radiat. Res.* 1963;18:272–6.

Berliner J A, Navab M, Fogelman A M, Frank J S, Demer L L, Edwards PA, Watson AD, Lusis A J. Atherosclerosis: basic mechanisms. Oxidation, inflammation, and genetics. *Circulation* 1995;91:2488–2496.

Buja L, Willerson JT, Roll of Inflammation in Coronary Plaque Disruption. (1994) *Circulation* 89, 2303–5.

Biffl W L, Moore E E, Moore F A, Barnett CC, Jr., Carl VS, Peterson V N. Interleukin-6 delays neutrophil apoptosis. *Archives of Surgery* 1996;131(1):24–9; discussion 29–30.

Blackburn M J, Wheldon T E, Field S B, Goldman J M. The sensitivity to hyperthermia of human granulocyte/macrophage progenitor cells (CDU-GM derived from blood or marrow of normal subjects and patients with chronic granulocytic leukaemia. *British J. of Cancer* 1984;506: 745–51.

Casscells W, Engler D, Willerson J T, Mechanisms of Restenosis, *Texas Heart Inst. J.* (1994) 21: 68–77.

Chen B D, Sapareto S A, Chou T H. Induction of prostaglandin production by hyperthermia in murine peritoneal exudate macrophages. *Cancer Res.* 1987;37(1):11–15.

Chen B D, Sapareto S A, Chou T H. Induction of prostaglandin production of hyperthermia in murine peritoneal exudate macrophages. *Cancer Res.* 1987;47(1):11–15.

Cohen D S, Palmer E, Welch W J, Sheppard D. The response of guinea pig airway epithelial cells and alveolar macrophages to environmental stress. *Am. HJ Resp. Cells and Molec. Bio.* 1991;5(2):133–43.

Elkon D, McGrath H E. Thermal inactivation energy of granulocyte-monocyte stem cells. *Radiat. Res.,* 1981;87: 367–72.

Ensor J E, Crawford E K, Hasday J D. Warming macrophages to febrile range destabilized tumor necrosis factor-a mRNA without inducing heat shock. *Am. J. Physiol* 269 (*Cell Physiol*.38) 1995:C1140–C1146.

Falk E, Shah P K, Fuster V, Coronary Plaque Disruption. *Circulation* 1995, 92 157–71.

Field S B, Morris C C. The relationship between heating time and temperature: its relevance to clinical hyperthermia. *Radiotherapy & Oncology* 1983; 1:179–186.

Fouqueray B, Phillipe C, Amrani A, Perez J, Baud L. Heat shock prevents lipopolysaccharide-induced tumor necrosis factor-alpha synthesis by rat mononuclear phagocytes. *Europ. J. Immunol.* 1992;22(11):2983–7.

Freeman M L, Raaphorst G P, Hopwood L E, Dewey W C. The effect of pH on cell lethality induced by hyperthermia treatment. *Cancer* 1980;45:2791–2300.

Gerweck L E, Dahlberg W K, Epstein L F, Shimm D S. Influence of nutrient and energy deprivation on cellular response to single and fractionated-heat treatments. *Radiat. Res.* 1984;99:573–81.

Hamilton R F Jr., Li L, Felder TB, Holian A. Bleomycin induces apoptosis in human alveolar macrophages. *Amer. J. Physiol.* 1995;269(3, Pt. 1):L318–25.

Haveman J, Hahn G M. The role of energy in hyperthermia-induced mammalian cell inactivation: a study of the effects of glucose starvation and an uncoupler of oxidative phosphorylation. *J. Cellular Physiol.* 1982;107:237–241.

Katsuda, S. Human Atherosclerosis. *Amer. J. Path.* 1993; 142:1787–93.

Kim Y M, de Vera M E, Watkins S C, Billiar T R. Nitric oxide protects cultured rat hepatocytes from tumor necrosis factor-alpha-induced apoptosis by inducing heat shock protein 70 expression. *J. Biological Chem.* 1997;272(2): 1402–11.

Klostergaard J, Bara M, Tomasovic S P. Hyperthermic modulation of tumor necrosis factor dependent, *Cancer Res.* 1989; 49: 6257–7.

Kobayashi E. Yamagishi M, Kamamoto Y, Yoshida Y, Uchimo H. Cell cycle-dependent heat sensitization of murine granulocyte-macrophage progenitor cells in regenerating marrow. *Cancer Res.* 1985;45(4):1459–63.

Kunkel S L, Wiggins E C, Chensue S W, Larrick J. *Biochem. Biophys. Res. Comm.* 1986;137:404–10.

Lavie L, Weinreb O, Gershon D. Age-related alterations in superoxide anion generation in mouse peritoneal macrophages studied by repeated stimulations and heat shock treatment. *J Cellular Physio.* 1992;152(2):382–8.

Mangan D F, Welch G R, Wahl SM. Lipopolysaccharide tumor necrosis factor alpha and IL-1 prevent programmed cell death (apoptosis) in human peripheral blood monocytes. *J. Immunol.* 1991;146:1541–46.

Morange M, Dubois M F F, Bensaude O, Lebou P. Interferon pretreatment lowers the threshold for maximal heat-shock response. *J. Cell Physiol.* 1986;127:417-.

Moreno P R, Fallon J., Shah P, Fuster V, Restenosis and Thrombosis Formation related to Macrophage Migration.

S. Nagata, P. Golstein, The Fas death factor. *Science* 1995; 267:1449–1455.

Nishina H, Fischer K D, Radvanyi L, Shahinian A, Hakem R, Rubie E A, Bernstein A, Mak T W, Woodgett J R, Penninger J M. Stress-signaling kinase Seki protects thymocytes from apoptosis mediated by CD95 and CD3. *Nature* 1997;385 (6614):350–3.

O'Hara M D, Xiong Q B, Boyer J W, Leeper D B. Intrinsic Thermal response, thermotolerance development and stepdown heating in murine bone marrow progenitor cells. *International J Hyperthermia* 1992;8(4):451–61.

Papadimitriou J M, van Bruggen I. Quantitative investigations of apoptosis of murine mononuclear phagocytes during mild hyperthermia. *Experimental & Molecular Pathol.* 1993;59(1):1–12.

Pizurk L, Polla B S. *J. Cell Physiol.* 1994;161:169–77.

Prins J B, Walker N I, Winterford C M, Cameron D P. Apoptosis of human adipocytes in vitro. *Biochemical and Biophysical Res. Comm.* 1994;201(2):500–7.

Raaphorst G P, Broski A P, Azzam E I. Sensitivity to heat, radiation and heat Plus radiation of Chinese hamster cells synchronized by mitotic selection, thymidine block or hydroxyurea block. *J. Therm. Biol.* 1986;10(3):177–181.

Reddy M V, Gangadharam P R. Heat shock treatment of macrophages causes increased release of superoxide anion. *Infection &Immunity* 1992;60(6):2386–90.

Ribeiro S P, Villar J, Downey GP, Edelson J E, Slutsky A S. Effects of the stress response in septic rats and LPS-stimulated alveolar macrophages: evidence for TNO-alpha posttranslation regulation. *Am. J. of Resp. and Critical Care Med* 1996;154(6 Pt 1):1843–50.

Ross R., The Pathogenisis of Atherosclerosis, *Nature* 1993, 362, 801–9.

Sivo J, Harmon J M, Vogen S N. Heat shock mimics glucocorticoid effects on IFN-gamma-induced Fc gamma RI and Ia messenger RNA expression in mouse peritoneal macrophages. *J Immunol.* 1996;156(9):3450–4.

Snyder Y M, Guthrie L, Evans G F, Zuckerman S H. Transcriptional inhibition of endotoxin-induced monokine synthesis following heat shock in murine peritoneal macrophages. *J Leukocyte Biol.* 1992;51(2):181–7.

Steller H, Mechanisms and genes of cellular suicide. Science 1995;267: 1445–1449 Thompson C B, Apoptosis in the pathogenesis and treatment of disease. *Science* 1995;267: 1456–1462.

Vaux D L, Strasser A, The molecular biology of apoptosis, *PNAS*(USA) 1996;93 :2239–2244

Verhelj M, Bose R, Xin X L, Yao B, Jarvis W D, Grant S, Birrer M J, Szolo E, Zon L I, Kynakis J M, Haimoritz-Friedman A, Furks Z, Kolesnik R N. Requirement for ceramide-initiated SAPKIJNK signalling in stress-induced apoptosis. *Nature* 1996;380:75–9.

Wang J H, Redmond H P Watson R W, Condron C, Bouchier-Hayes D. Induction of heat shock protein 72 prevents neutrophil-mediated human endothelial cell necrosis. *Archives of Surg* 1995; 130(12):1260–5.

Wang J H, Redmond HP, Watson R W, Bouchier-Hayes D. Induction of human endothelial cell apoptosis required both heat shock and oxidative stress responses. *Amer. J. Physiol.* 1997;272(5 Pt 1):C1543–51.

Westra A and Dewey W C. Variation in sensitivity to hear shock during the cell cycle of Chinese hamster cells in vitro. *International J. Radiat. Biol.* 1971; 19:467–77.

Wike-Hooly, Haveman J, Reinhold H S. The relevance of tumor pH to the treatment of malignant disease. *Radiotherapy &Oncology* 1984;2:343–66.

William R, Watson G, Redmond HP, Wang J H, Bouchier-Hayes D. Bacterial ingestion, tumor necrosis factor-alpha, and heat induced programmed cell death in activated neutrophils. *Shock* 1996;5(1):47–51.

What is claimed is:

1. A method of treating inflammation comprising heating inflamed tissue at a temperature below 50° C. for about 10–15 seconds, such that said heating induces apoptosis in immune cells, wherein said inflamed tissue comprises an atherosclerotic plaque.

2. The method of treating inflammation of claim 1 wherein said heating is accomplished by a heat source positioned within the lumen of a blood vessel.

3. The method of treating inflammation of claim 2 wherein said heat source comprises a stent.

4. The method of treating inflammation of claim 3 wherein the said stent is heated by microwave radiation.

5. The method of treating inflammation of claim 3 wherein the said stent is heated by radiofrequency radiation.

6. The method of treating inflammation of claim 1 wherein said with a heat source comprising a catheter.

7. The method of treating inflammation of claim 1 wherein said a heat source comprising infrared radiation.

8. The method of treating inflammation of claim 1 further comprising treating said inflamed tissue with at least one chemical agent.

9. The method of treating inflammation of claim 8 wherein said chemical agent is a cytokine.

10. The method of treating inflammation of claim 8 wherein said chemical agent is a growth factor.

11. The method of treating inflammation of claim 10 wherein said growth factor is selected from the group consisting of insulin-like growth factor, vascular endothelial growth factor, fibroblast growth factor.

12. The method of treating inflammation of claim 1 further comprising treating said inflamed tissue with gamma-radiation.

13. The method of treating inflammation of claim 1 wherein said heating step further comprises treating said inflamed tissue with radiofrequency.

14. The method of treating inflammation of claim 1 further comprising treating said inflamed tissue with ultraviolet radiation.

15. The method of treating inflammation of claim 1 wherein said heating step further comprises treating said inflamed tissue with microwave radiation.

16. The method of treating inflammation of claim 1 wherein said heating step further comprises treating said inflamed tissue with a heated liquid.

17. A method of treating an atherosclerotic plaque comprising heating an inflamed atherosclerotic plaque in the lumen of a blood vessel with a heat source having a temperature in the range of from about 38.5° C. to 44° C. for a period of time ranging from about 15 to 60 minutes and inducing apoptosis in a macrophage.

18. A method of inducing apoptosis in inflammatory cells associated with an inflamed plaque wherein said inflammatory cells are heated for fifteen (15) minutes.

19. A method of inducing apoptosis in inflammatory cells associated with an inflamed plaque wherein said inflammatory cells are heated at a temperature of between approximately 41° C. and 44° C.

* * * * *

UNITED STATES PATENT AND TRADEMARK OFFICE
CERTIFICATE OF CORRECTION

PATENT NO.       : 7,123,968 B1
APPLICATION NO.  : 09/303313
DATED            : October 17, 2006
INVENTOR(S)      : S. Ward Casscells, III and James T. Willerson It is certified that error appears in the above-identified patent and that said Letters Patent is hereby corrected as shown below:

In column 1, between lines 10 and 15: Insert

--STATEMENT REGARDING FEDERALLY
SPONSORED RESEARCH OR DEVELOPMENT

The U.S. Government has a paid-up license in this invention and the right in limited circumstances to require the patent owner to license others on reasonable terms as provided for by the terms of DAMD17-98-1-8002 awarded by the Army/MRMC.--.

Signed and Sealed this

Ninth Day of December, 2008

JON W. DUDAS
*Director of the United States Patent and Trademark Office*